United States Patent [19]

Nicksic

[11] 4,415,671
[45] Nov. 15, 1983

[54] METHOD FOR MODIFYING ELECTRON SPIN RESONANCE SIGNALS FROM HYDROCARBON CRUDE

[75] Inventor: Stephen W. Nicksic, Brea, Calif.

[73] Assignee: Chevron Research Company, San Francisco, Calif.

[21] Appl. No.: 202,102

[22] Filed: Oct. 30, 1980

[51] Int. Cl.³ .......................................... G01N 24/10
[52] U.S. Cl. ................................ 436/29; 324/316; 436/139; 436/173
[58] Field of Search .................... 23/230 EP, 230 HC; 324/300, 303, 316, 323, 324; 436/60, 173, 139, 29

[56] References Cited

U.S. PATENT DOCUMENTS 3,060,371 10/1962 Townsend et al. ................. 324/0.5
3,719,453 3/1973 Erdman ............................. 23/230 EP
3,740,641 6/1973 Hwang et al. ................... 23/230 EP

OTHER PUBLICATIONS

Niizuma et al. *Fuel*, 1977, vol. 56, Jul. pp. 249–256.
Yen et al., *Analytical Chemistry*, vol. 34, No. 6, May 1962, pp. 694–700.
Saraceno et al., *The Journal of Chemical Physics*, vol. 34, No. 1, Jan. 1961, pp. 260–263.

*Primary Examiner*—Arnold Turk
*Attorney, Agent, or Firm*—D. A. Newell; G. W. Wasson; L. S. Gruber

[57] ABSTRACT

Method for enhancing electron spin resonance signals from crude petroleum by contacting the crude petroleum with a chemical which effects the population of free radical asphaltenes in the crude petroleum. The enhancement is in a positive sense when the chemical is a halogen and particularly iodine. The enhancement is in a negative sense (suppression) when the chemical is ferric chloride.

8 Claims, 2 Drawing Figures

CRUDE OIL/ENHANCED CRUDE OIL

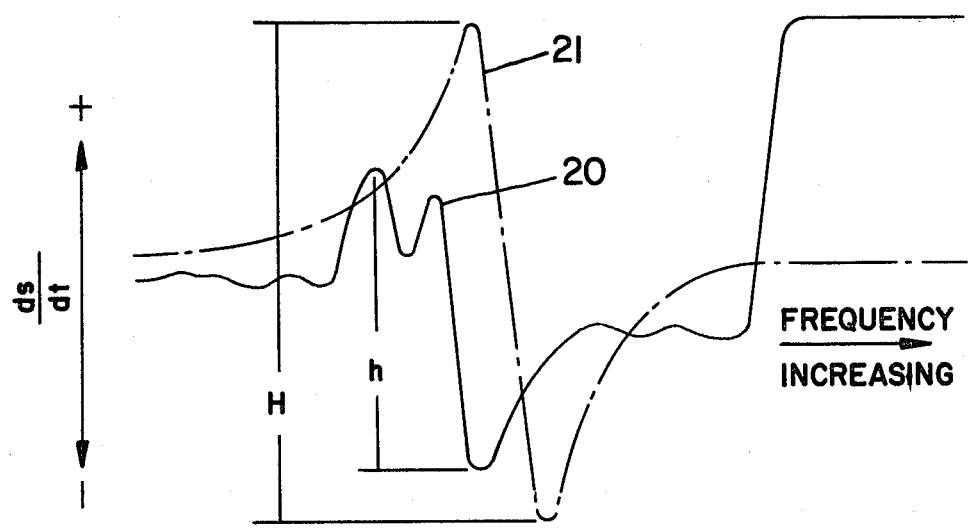
CRUDE OIL/ENHANCED CRUDE OIL
FIG _ 1
REFINED PRODUCT
NO EVIDENCE OF ENHANCEMENT
FIG _ 2

METHOD FOR MODIFYING ELECTRON SPIN RESONANCE SIGNALS FROM HYDROCARBON CRUDE

BACKGROUND OF THE INVENTION

1. Field of the Invention

This invention relates to a method for identifying hydrocarbon crude oil constituents and more particularly, to a method for identifying hydrocarbon crude oil by electron spin resonance signals.

It has been known for some time that most crude oils exhibit electron spin resonance so that the presence of these crude oils may be detected by measurements of the resonant absorption of energy from a radio frequency electromagnetic field encompassing a sample. With presently available laboratory apparatus, both qualitative and quantitative analysis may be made of samples through electron paramagnetic resonance measurements of absorption of radio frequency electromagnetic energy in magnetic fields. Simply stated, the energy absorbed in these analyses is absorbed at the frequency of precession of almost free electrons in the crude oil sample. The free radicals that exhibit the absorption of this radio frequency energy are characteristic of certain chemical structures and are peculiarly present in the chemical structures of crude oil. The free radicals exhibit the property of having a magnetic moment because of uncompensated electron spin; hence, they are paramagnetic.

Many other materials also exhibit electron spin resonance and, unfortunately, some of these many other materials may be found in their natural state in association with petroleum crude. While it may be possible to distinguish between the electron spin resonance signals of crude oil from the electron spin resonance signals of other materials, such distinguishing techniques are frequently elaborate laboratory procedures that must be performed with carefully controlled laboratory equipment. To avoid the confusion between electron spin resonance signals from crude oils and similar signals from other materials, it is therefore desirable to develop a simple technique which may be used to distinguish the two signal sources.

A further confusion as to the source of electron spin resonance signals can exist when making measurements within or along a well bore penetrating an earth formation because electron spin resonance signals may be produced from crude oils as well as from heavy hydrocarbon refined products. Electron spin resonance signals may be derived from the heavy ends of refined products such as residuum or possibly from some heavy gas oils, but will not be derived from diesel, gas, butane or other light ends. Such heavy refined products might exist along a well bore in the form of oil based drilling muds or from other hydrocarbons used in drilling fluids. It is therefore an additional desire to provide a method that will permit a distinction to be made between signals derived from crude hydrocarbons and signals derived from refined hydrocarbon products.

2. Prior Art

As so far as I am aware, no prior art exists for the technique that is herein disclosed. U.S. Pat. No. 3,060,371, J. Townsend et al, issued Oct. 23, 1962, For Geological Prospecting Process and Apparatus, discloses an early concept of the geological prospecting process wherein electron spin resonance signals from unpaired electrons in carbonaceous materials may be detected and used in the prospecting process. Later investigators have suggested the use of electron paramagnetic resonance signal measurements from crude oils as a means for identifying the presence of crude oil along subsurface earth formations. One such disclosure is found in U.S. application Ser. No. 745,959, of Robert R. Unterberger, filed July 1, 1958, For Electron Paramagnetic Resonance Well Logging, now abandoned, wherein a technique is described for measuring electron paramagnetic resonance signals along the bore of a well penetrating an earth formation. Other investigators have suggested the enhancement of electron paramagnetic signals by subjecting the unpaired electrons to additional radiation; however, such enhancement techniques require elaborate laboratory equipment and it is substantially impossible to perform these techniques within a well bore within an earth formation.

The object of the present invention is to provide a simple enhancement mechanism for improving the electron spin resonance signals derived from hydrocarbon crude oil and for distinguishing the electron spin resonance signals from crude oil from those signals which could be derived from most refined hydrocarbon products, coal or shale.

A further object of the present invention is a simple and inexpensive method for suppressing the electron spin resonance signals from crude petroleum.

Further objects and features of the present invention will be readily apparent to those skilled in the art from the appended drawings and specification describing the preferred techniques in accordance with the foregoing objects.

BRIEF DESCRIPTION OF THE DRAWINGS

FIG. 1 is a time vs. signal strength curve illustrating electron spin resonance signals produced in accordance with the present invention.

FIG. 2 is a time vs. signal strength curve of electron spin resonance signals from a refined hydrocarbon product produced in accordance with the present invention.

DETAILED DESCRIPTION OF THE INVENTION

I have discovered that electron spin resonance signals from the unpaired electrons in hydrocarbon crudes may be enhanced by measuring the electron spin resonance signals in an environment containing iodine. I have further discovered that electron spin resonance signals from petroleum crudes may be suppressed by measuring the electron spin resonance signals in an environment containing ferric chloride.

In FIG. 1, representative electron spin resonance signals are shown with the first signal 20 being that derived from a hydrocarbon crude oil and having a height represented by the small letter h. In that same figure, an electron spin resonance signal 21 is shown from the same hydrocarbon crude when measured in an environment containing iodine. In that case, the height of the signal is represented by the large letter H. The increase in amplitude, the enhancement, of the second signal is attributable to the presence of iodine.

In FIG. 2, electron spin resonance signals from refined petroleum products are shown with signal 30 being the basic signal and signal 31 being the signal produced with the product in the presence of iodine.

Both signals were produced under the same conditions as those produced in FIG. 1.

It should be observed that the signal from the unrefined sample in FIG. 1 is much larger than the signal of the refined sample in FIG. 2. This difference is because the signal is from the asphaltic constituent of the sample which is substantially removed from the sample in a refining process. It should also be observed that the enhancement of the signal due to the presence of iodine is only observed when asphaltic materials are present; thus, no enhancement of the signal in FIG. 2.

While iodine is the recommended material for use in enhancing the ESR signal, other halogens, such as chlorine or bromine, will be effective. Iodine is the preferred halogen because it is readily introduced into contact with the sample when ESR signals are being measured with laboratory equipment. Further, iodine is a relatively safe material for use around petroleum products, is easily available in desirable solutions at desirable concentrations, and is long lasting in the uses contemplated here.

It is my belief that the enhancement phenomenon of iodine on the ESR signal from asphaltic material is due to an oxidizing effect of the iodine on the crude oil sample. That oxidizing process removes electrons from the asphaltene and makes more free radical asphaltenes available. The oxidation results in a shift towards the "keto" form of compounds which exist in a keto/enol resonance condition. It is the presence of these free radical asphaltenes that is represented in the ESR signal. The magnitude of the signal is representative of the quantity of free radical material present.

In accordance with my discovery, ESR signals from crude oils containing asphaltenes can be enhanced by subjecting the sample to an environment containing iodine. The existence of the enhancement may be used to identify the presence of asphaltic material and to distinguish crude hydrocarbons from refined hydrocarbons. The amount of original ESR signal can be used as a quantitative measure, of the amount of asphaltic material present and a qualitative indication of the kind of or source of the crude oil present.

I have also observed the suppression of ESR signals from asphaltic material by subjecting the sample to the presence of ferric chloride. The explanation for this suppression is thought to be as follows: The stable resonance form of asphaltenes is intermediate between "keto" and "enol" forms in aromatic structures (rings), the keto form having unpaired electrons. Ferric chloride, a classical reagent for phenolic hydroxyl, shifts the equilibrium away from the keto form, thereby reducing the free radical population. The ferric chloride will normally be added in a solution form with benzene, toluene, xylene or carbon tetrachloride.

I have observed this suppression of ESR signals only on hydrocarbon crudes; it does not occur when measuring signals from hydrocarbons in coal, shale, or in most refined hydrocarbon products. This phenomenon may be used to identify the presence of asphaltenes and to distinguish crude hydrocarbons from most refined hydrocarbons.

While certain preferred embodiments of the invention have been specifically disclosed, it should be understood that the invention is not limited thereto as many variations will be readily apparent to those skilled in the art and the invention is to be given its broadest possible interpretation within the terms of the following claims.

What is claimed is:

1. A method for enhancing electron spin resonance signals from crude petroleum comprising contacting said samples with a halogen or ferric chloride to affect the number of the population of free radical asphaltenes in said crude petroleum while detecting said electron spin resonance signals.

2. The method of claim 1 wherein ferric chloride is added to decrease the population of free radicals and suppress the detected electron spin resonance signal.

3. The method of claim 2 wherein said ferric chloride is in a solution from the group including benzene, toluene, xylene, or carbon tetrachloride.

4. The method of claim 1 wherein halogen is added to increase the population of free radicals and enhance the detected electron spin resonance signals.

5. The method of claim 4 wherein said halogen is iodine.

6. The method of claim 5 wherein said iodine is a fluid solution.

7. The method of claim 4 wherein said crude petroleum is associated with samples of earth formations in which crude petroleum has been present and said samples are contacted with said enhancing halogen to distinguish electron spin resonance signals from electrons within crude petroleum on said sample from electron spin resonance signals from electrons within said earth formation constituent materials.

8. The method of claim 7 wherein a quantitative measure of crude petroleum within said earth formation sample is made by measuring the magnitude of enhancement of said electron spin resonance signal in response to contacting said earth formation sample with said halogen.

* * * * *